United States Patent
Kalloo et al.

(10) Patent No.: US 7,721,742 B2
(45) Date of Patent: May 25, 2010

(54) METHODS FOR DIAGNOSTIC AND THERAPEUTIC INTERVENTIONS IN THE PERITONEAL CAVITY

(75) Inventors: Anthony Nicolas Kalloo, Baltimore, MD (US); Sergey Veniaminovich Kantsevoy, Silver Spring, MD (US)

(73) Assignee: Johns Hopkins University, Baltimore, MD (US)

( * ) Notice: Subject to any disclaimer, the term of this patent is extended or adjusted under 35 U.S.C. 154(b) by 1116 days.

(21) Appl. No.: 09/815,336

(22) Filed: Mar. 23, 2001

(65) Prior Publication Data

US 2001/0049497 A1 Dec. 6, 2001

Related U.S. Application Data

(60) Provisional application No. 60/191,764, filed on Mar. 24, 2000.

(51) Int. Cl.
- *A61B 19/00* (2006.01)
- *A61B 18/18* (2006.01)
- *A61M 29/00* (2006.01)

(52) U.S. Cl. .......................... 128/898; 606/10; 606/47; 600/116; 604/96.01; 604/101.01; 604/101.05

(58) Field of Classification Search ......... 600/102–104, 600/108, 113–116, 121–125, 129–156; 604/27–45, 604/500, 95.01, 95.03, 96.01, 101.01–106.05, 604/121, 174, 50, 131, 139; 606/10–13, 606/42–52; 128/898

See application file for complete search history.

(56) References Cited

U.S. PATENT DOCUMENTS

| 3,774,608 | A | | 11/1973 | Wohler | |
|---|---|---|---|---|---|
| 3,915,171 | A | * | 10/1975 | Shermeta | 604/101.05 |
| 4,249,535 | A | | 2/1981 | Hargest | |
| 4,315,509 | A | | 2/1982 | Smit | |
| 4,327,736 | A | * | 5/1982 | Inoue | 604/101.05 |

(Continued)

FOREIGN PATENT DOCUMENTS

WO  WO 96/24296  8/1996

OTHER PUBLICATIONS

Abstract; Kalloo AN, Kantsevoy SV, Singh VK, Magee CA, Vaughn CA, Hill SL, "Flexible transgastric peritoneoscopy; a novel approach to diagnostic and therapeutic interventions in the peritoneal cavity"; Gastroenterology 2000; 118: A1039.

(Continued)

*Primary Examiner*—David Shay
(74) *Attorney, Agent, or Firm*—Nixon & Vanderhye P.C.

(57) ABSTRACT

A novel approach to diagnostic and therapeutic interventions in the peritoneal cavity is described. More specifically, a technique for accessing the peritoneal cavity via the wall of the digestive tract is provided so that examination of and/or a surgical procedure in the peritoneal cavity can be conducted via the wall of the digestive tract with the use of a flexible endoscope. As presently proposed, the technique is particularly adapted to transgastric peritoneoscopy. However, access in addition or in the alternative through the intestinal wall is contemplated and described as well. Transgastric and/or transintestinal peritoneoscopy will have an excellent cosmetic result as there are no incisions in the abdominal wall and no potential for visible post-surgical scars or hernias.

21 Claims, 14 Drawing Sheets

U.S. PATENT DOCUMENTS

| | | | |
|---|---|---|---|
| 4,538,606 A | | 9/1985 | Whited |
| 4,664,114 A | | 5/1987 | Ghodsian |
| 4,676,778 A | | 6/1987 | Nelson |
| 4,773,394 A | | 9/1988 | Reichstein |
| 4,913,142 A | | 4/1990 | Kittrell et al. |
| 5,002,532 A | | 3/1991 | Gaiser |
| 5,297,536 A | * | 3/1994 | Wilk .................. 600/139 |
| 5,389,074 A | | 2/1995 | Parker |
| 5,400,770 A | | 3/1995 | Nakao |
| 5,458,583 A | * | 10/1995 | McNeely et al. ....... 604/103.13 |
| 5,514,091 A | | 5/1996 | Yoon |
| 5,599,294 A | | 2/1997 | Edwards |
| 5,599,300 A | | 2/1997 | Weaver |
| 5,656,013 A | | 8/1997 | Yoon |
| 5,665,062 A | | 9/1997 | Houser |
| 5,665,103 A | | 9/1997 | Lafontaine |
| 5,672,153 A | | 9/1997 | Lax |
| 5,704,908 A | | 1/1998 | Hofmann |
| 5,713,942 A | | 2/1998 | Stern |
| 5,730,725 A | | 3/1998 | Yoon |
| 5,735,817 A | | 4/1998 | Shantha |
| 5,775,338 A | | 7/1998 | Hastings |
| 5,779,688 A | | 7/1998 | Imran |
| 5,779,698 A | | 7/1998 | Clayman |
| 5,782,800 A | | 7/1998 | Yoon |
| 5,782,812 A | | 7/1998 | Hart |
| 5,797,960 A | | 8/1998 | Stevens |
| 5,800,378 A | | 9/1998 | Edwards |
| 5,803,919 A | | 9/1998 | Hart |
| 5,829,447 A | | 11/1998 | Stevens |
| 5,846,182 A | | 12/1998 | Wolcott |
| 5,855,614 A | | 1/1999 | Stevens |
| 5,865,176 A | | 2/1999 | O'Neil |
| 5,876,325 A | * | 3/1999 | Mizuno et al. .............. 600/107 |
| 5,876,369 A | | 3/1999 | Houser |
| 5,904,698 A | | 5/1999 | Thomas |
| 5,906,579 A | * | 5/1999 | Vander Salm et al. .......... 606/2 |
| 5,924,424 A | | 7/1999 | Stevens |
| 5,951,513 A | | 9/1999 | Miraki |
| 6,030,365 A | * | 2/2000 | Laufer ..................... 604/174 |
| 6,156,006 A | * | 12/2000 | Brosens et al. .............. 604/104 |
| 6,689,062 B1 | | 2/2004 | Mesallum |
| 2004/0097801 A1 | | 5/2004 | Mesallum |

OTHER PUBLICATIONS

Best of DDW 2002; "Reviews in Gastroenterological Disorders"; vol. 2, No. 3: 2002; pp. 126-141.

Kalloo et al; "Flexible transgastric peritoneoscopy; a novel approach to diagnostic and therapeutic interventions in the peritoneal cavity"; Gastrointestinal Endoscopy; vol. 59; No. 8: 2004; pp. 1-4 (Article in Press).

Editorial; Hochberger et al.; "Transgastric Surgery in the Abdomen: the Dawn of a New Era?"; American Society for Gastrointestinal Endoscopy; vol. 62; No. 2: 2005; 293-296.

Kalloo et al.; **579; "Endoscopic Gastrojejunostomy with Long-Term Survival in a Porcine Model"; Gastrointestinal Endoscopy; vol. 55, No. 5, 2004; 1 page.

U.S. Appl. No. 10/700,133, filed Nov. 2, 2003.

U.S. Appl. No. 11/050,284, filed Feb. 3, 2005.

Kalloo et al; "Flexible transgastric peritoneoscopy; a novel approach to diagnostic and therapeutic interventions in the peritoneal cavity"; Gastrointestinal Endoscopy; vol. 60; No. 1: Jul. 2004; pp. 114-118.

Bard® Eliminator® Pet Biliary Balloon Dilators Brochure; Bard Interventional Products Division; Apr. 1997; 3 pages.

Cook® Wilson-Cook Medical GI Endoscopy; Huibregtse® Needle Knife Papillotomes; 6 pages; 1999.

Bard Interventional Products Division; Bard® Eliminator® PET-Biliary Balloon Dilators; 3 pages; 1997.

* cited by examiner

METHODS FOR DIAGNOSTIC AND THERAPEUTIC INTERVENTIONS IN THE PERITONEAL CAVITY

This application claims the benefit of U.S. Provisional Application Ser. No. 60/191,764, which was filed Mar. 24, 2000, the disclosure of which is incorporated herein by this reference.

BACKGROUND OF THE INVENTION

1. Field of the Invention

The present invention relates to a procedure for accessing and examining and/or conducting surgical procedures in a body cavity, such as the peritoneal cavity, and instruments adapted therefor.

2. Description of the Related Art

The traditional approach to the peritoneal cavity is by trans-abdominal wall incision. More recently, the less invasive laparoscopic surgical technique has been used to access and examine the peritoneal cavity. Laparoscopy is currently performed via small incisions made through the anterior abdominal wall. Via these incisions, a rigid laparoscope is introduced, as are various microsurgical instruments if a procedure is performed within the peritoneal cavity. Laparoscopy is therefore a surgical procedure and carries the risk of infection of the skin incisions and possible development of post-operative hernias, and/or scars which may create cosmetic defects.

BRIEF SUMMARY OF THE INVENTION

We have developed a novel approach to diagnostic and therapeutic interventions in the peritoneal cavity. More specifically, we have developed a technique for accessing the peritoneal cavity via the wall of the digestive tract so that examination of and/or a surgical procedure in the peritoneal cavity can be conducted via the wall of the digestive tract with the use of a flexible endoscope. As presently proposed, the technique is particularly adapted to transgastric peritoneoscopy. However, access in addition or in the alternative through another wall of the digestive tract, such as the intestinal wall or the esophageal wall, is contemplated and described generally as well. Transgastric and/or transintestinal peritoneoscopy will have an excellent cosmetic result as there are no incisions in the abdominal wall and no potential for visible post-surgical scars or hernias.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
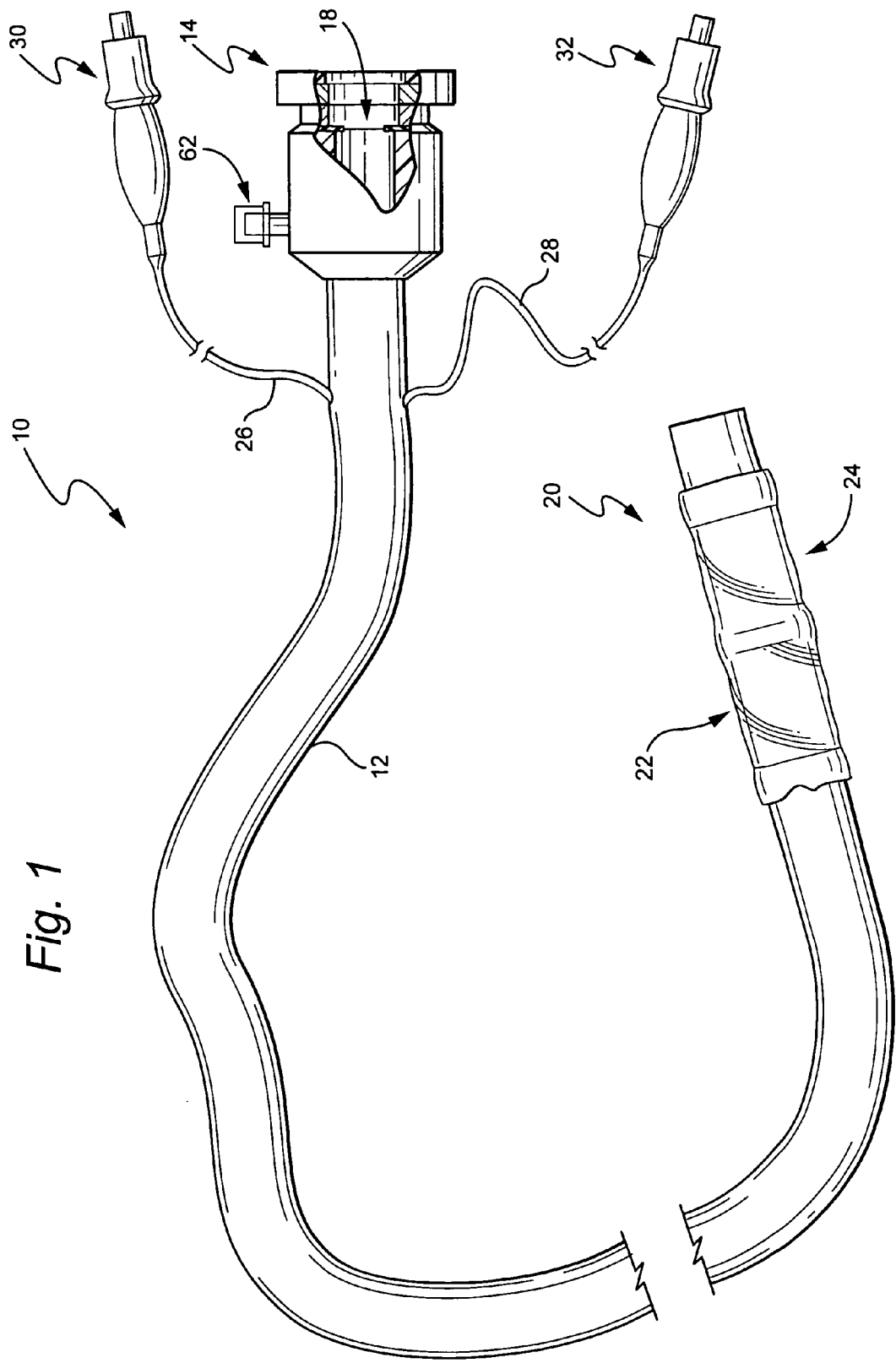
FIG. 1 is an illustration of an overtube according to an embodiment of the invention, with balloons deflated.
Figure 2:
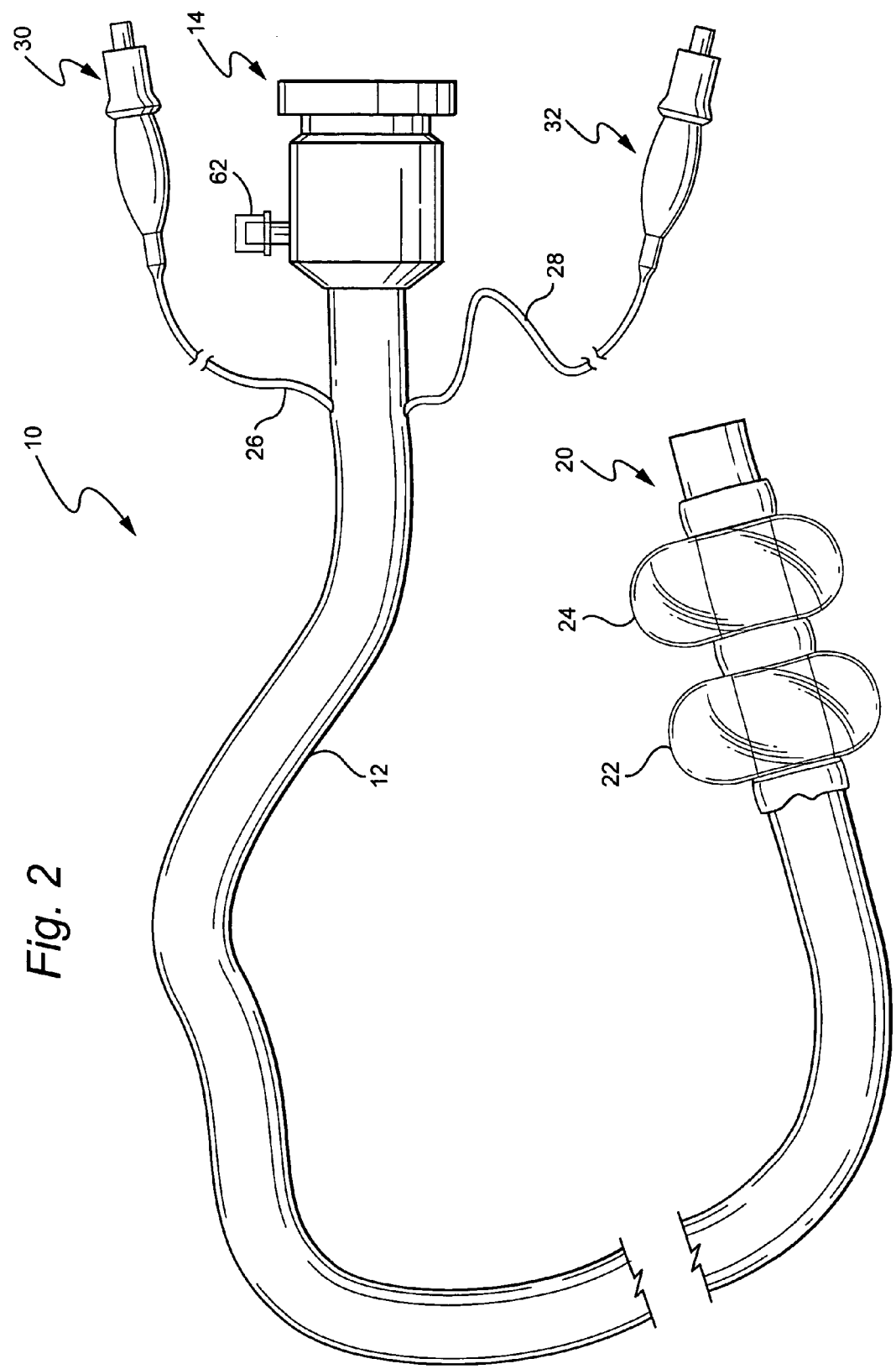
FIG. 2 is a view similar to FIG. 1 with the balloons inflated.

We have developed a new approach for the examination of the peritoneal cavity that uses a flexible endoscope and a specially adapted sterile overtube with anchoring balloons. The endoscopic procedure of the invention proposes to access the peritoneal cavity for examination and/or for the conduct of select surgical procedures via an incision through a wall of the digestive tract. The invention is described in greater detail herein below with reference in particular to peritoneal access through the stomach wall via the esophagus. However, as will be understood by those skilled in this art, using our approach, the peritoneal cavity can be accessed in addition or in the alternative via the intestinal wall and, depending upon the locus of the target access point(s), an esophageal approach and/or a colorectal approach can be adopted. In addition, the thoracic cavity may be approached through the esophagus or stomach.

This novel endoscopic procedure will be described herein below with reference to instruments and devices, some of which have been developed specifically for the implementation of this procedure. While some of the devices described herein are particularly adapted to this procedure, it is to be understood that commercial available devices may also be used to advantage to implement the process of the invention. Therefore, the endoscopic procedure of the invention is not to be limited to the use of a particular instruments described herein. The provision and use of devices specially adapted to this procedure may, however, facilitate its successful implementation. As will also be appreciated and understood from the disclosure to follow, the instruments developed for the implementation of this procedure may also be used to advantage in the conduct of other medical procedures. Thus, those novel instruments are not to be construed as limited to the uses therefor described herein with reference to transgastric peritoneoscopy.

As noted above, the invention provides a novel approach to the peritoneal cavity via the digestive tract. A transgastric approach is described in particular herein below, by way of example. Those skilled in the art will appreciate, however, how the techniques described herein can be applied to peritoneal access through other portions of the digestive tract and/or achieved via a colorectal approach. Accordingly a detailed description of such alternatives is omitted. Nevertheless, the invention is not to be limited to the presently proposed and preferred transgastric approach.

To access and examine the peritoneal cavity via the digestive tract in accordance with the present invention, a passage for the sterile insertion of an endoscope and/or various surgical instruments must be provided that isolates the peritoneal cavity from the interior of the digestive tract, such as the gastric cavity. Such a sterile pathway is provided in the presently preferred embodiment of the invention by providing a special, sterile overtube 10 having a conduit 12 that is sized to receive an endoscope therethrough and is flexible so as to be capable of flexing with the endoscope to navigate the digestive tract and be conducted and directed to a target access point on, e.g., the stomach wall. Typical endoscopes have an outer diameter on the order of about 10-15 mm. Accordingly, the overtube 10 preferably has in interior passage for the endoscope having a diameter of at least about 10 mm and preferably in the range of about 10-20 mm.

To allow visualization of the vicinity of the distal end of the overtube from within the overtube 10, via the endoscope, during the insertion of the overtube, incision of the stomach wall, and anchoring of the overtube, as described in greater detail herein below, in the presently preferred embodiment of the invention at least a distal portion 20 of the overtube 10 is formed from a transparent material. For ease of manufacture, the entire overtube conduit 12 may be advantageously formed from a transparent material.

The proximal end of the overtube 10 is provided with a valve housing 14 that includes a chamber 16 through which the endoscope passes into the lumen of the overtube conduit. The housing is configured to provide structural support for a valve/seal mechanism shown generally at 18. It is the function of the seal to prevent the escape of pressurized fluid through the overtube conduit 12 following insufflation to expand the peritoneal cavity for adequate examination. Any valve structure or mechanism now known or later developed to effect a seal about an endoscope or other instrument inserted through an access port to minimize escape of pressurized fluid can be provided to advantage at the proximal end of the overtube 10. In an exemplary embodiment, a suitable valve includes an aperture or septum seal having an aperture that allows it to receive and closely engage the outer surface of an endoscope inserted therethrough to form an airtight seal around the endoscope in operative use. This valve is formed from elastomeric material so that the aperture is biased to seal against the outer surface of the endoscope. In order to avoid significant friction forces, the aperture is preferably sized to a diameter slightly less then the outer diameter of the endoscope to be inserted therethrough. To accommodate a variety of instruments, however, the size of the aperture is preferably expandable without inducing substantial frictional forces to accommodate the various instrument sizes. Although a valve having a expandable aperture has been mentioned in particular above, it is to be understood that a zero closure valve may be provided in stead of or in addition to such an apertured sealing member.

The distal end 20 of the overtube is adapted to be anchored to the wall of, e.g., the stomach, at least during the peritoneoscopy and associated surgical procedure(s), if any, to provide a continuous path to and into the peritoneal cavity and to isolate the peritoneum from the gastric cavity. Such an anchoring and sealing function is provided in accordance with an exemplary embodiment of the invention by providing a pair of anchoring cuffs or balloons 22, 24 adjacent the distal end of the overtube. To selectively inflate and deflate the balloons, an inflation passage (not shown) for each balloon is defined longitudinally of the overtube, terminating proximally in respective inflation lines 26, 28 and inflation ports 30, 32. The inflation passages can be defined within the overtube wall or so as to extend along the interior or exterior surface of the overtube in a known manner.

Thus, as described in greater detail herein below, the distal end of the overtube is inserted through an incision formed in the gastric wall and the anchoring balloons provided adjacent the distal end are inflated, with one inside the peritoneal cavity and the other one inside the stomach. The more proximal balloon 22 may be inflated first to preclude over insertion of the overtube at the outset. The inflated balloons anchor the distal end 20 of the overtube 10 to the gastric wall to prevent the overtube from migrating further into the peritoneal cavity or back into the stomach and isolate the peritoneal cavity from the gastric cavity. The overtube thus disposed advantageously provides a conduit for manipulations inside the peritoneal cavity. Accordingly, a flexible endoscope can be advanced through the overtube into the peritoneal cavity for diagnostic examination and/or surgical manipulations. After the procedure has been completed, the anchoring balloons are deflated and the overtube and endoscope pull back into the stomach. As described in greater detail herein below, the remaining incision in the gastric wall is then closed. Most preferably, the incision in the gastric wall is closed with endoscopic clips delivered via the endoscope. In the alternative, sutures or other ligatures can be applied to close the incision, again most preferably using suitable microdevices fed through lumens therefor in the endoscope.

Figure 6:
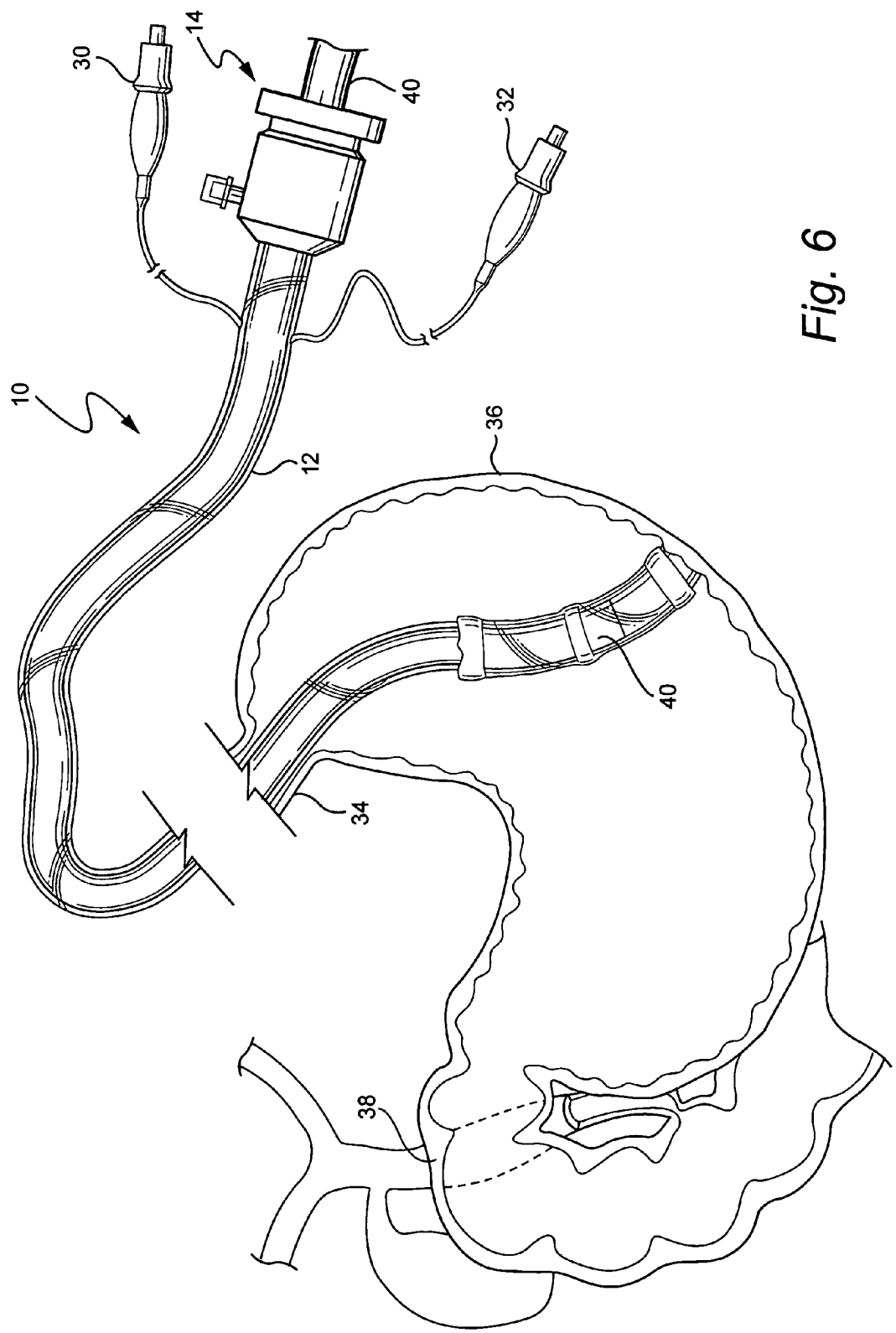
FIG. 6 is a schematic view showing the overtube with endoscope disposed therewithin located to a target portion of the stomach wall via the esophagus.

Referring to FIG. 6, a portion of the digestive tract including the distal end of the esophagus 34, the stomach 36, and the duodenum 38 are schematically shown as is an overtube 10 that has been fed through the esophagus 34 to terminate distally adjacent a target portion of the gastric wall. The overtube is desirably guided and directed into and within the stomach, in this example, or other segment of the digestive tract, with the aid of an endoscope 40 coaxially disposed therewithin.

As suggested above, to access the peritoneal cavity via the digestive tract, it is necessary to penetrate the wall of, e.g., the stomach. Desirably, the penetrating incision of the wall is made endoscopically by passing a suitable instrument through an accessory channel of the endoscope so that the procedure can be observed through the endoscope. Furthermore, desirably the incision is made as small as possible to facilitate the closure of the incision at the conclusion of the procedure, and is made in such a manner as to minimize bleeding.

In view of the objective of providing as small an incision as possible and the need to accommodate the overtube, an instrument for dilating the incision is preferably provided. The incising and dilating steps or functions may be provided by separate instruments. However, to facilitate the procedure, we have developed a combined incising and dilating device 42 that can be used to substantial advantage in the practice of the invention. The conduct of the incising and dilating processes using independent instruments and using our novel incising and dilating instrument will each be described herein below.

Figure 3:
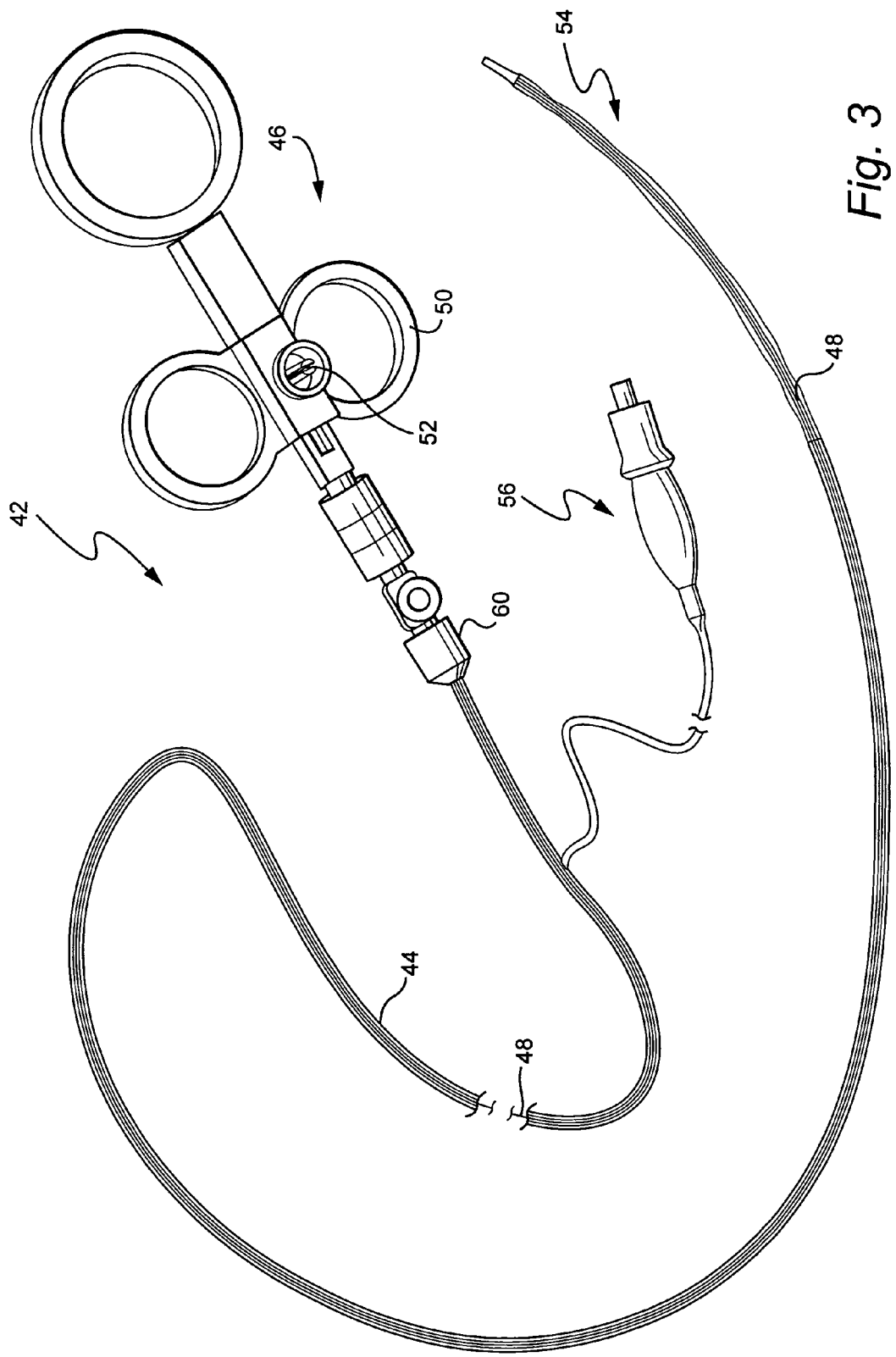
FIG. 3 is an illustration of a dilating needle-knife device according to an embodiment of the invention, with balloon deflated and needle retracted.
Figure 4:
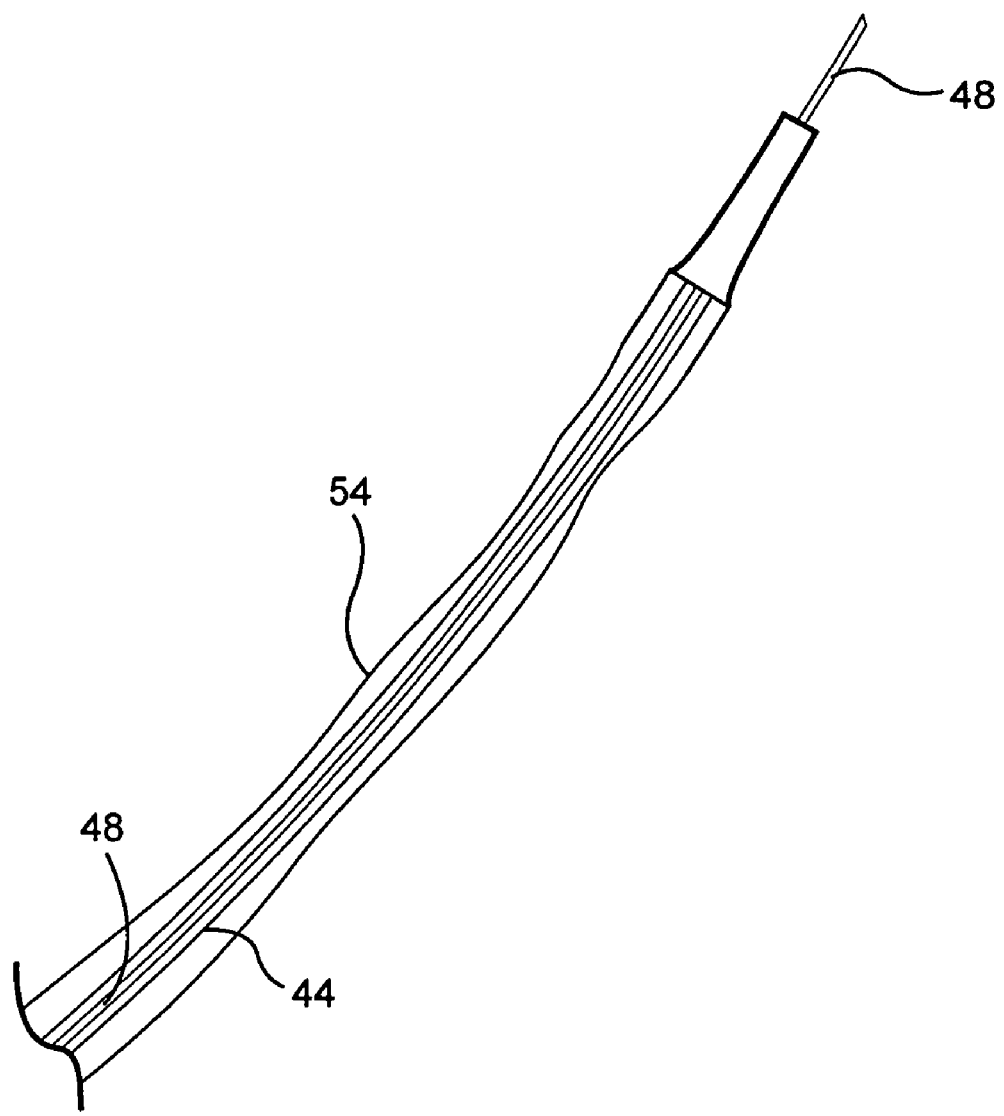
FIG. 4 is an enlarged view of the tip of the needle-knife device of FIG. 3 with the needle extended.

A dilating needle-knife device 42 for sequential incision and dilation to provide access through the wall of an organ or body passage is illustrated by way of example in FIGS. 3-5 and 7-9, in particular. The dilating needle-knife device 42 we have provided includes an elongated conduit 44 having proximal and distal ends. A needle-knife actuator 46 is mounted to the proximal end and a wire or needle-knife 48 extends therefrom longitudinally of the device to terminate adjacent the distal end of the elongate conduit. The needle-knife actuator 46 includes a slide trigger 50 that is secured to the proximal end of the needle-knife wire for selectively projecting the needle-knife 48 as shown in FIG. 4 and retracting the needle-knife as shown in, e.g., FIG. 3. An electrical coupler 52 is provided on the needle-knife actuator 46, more specifically on the trigger 50, for electrically coupling the needle-knife wire 48 to a current source (not shown). Electrification of the needle-knife can be selectively accomplished by a foot pedal switch or the like (not shown), in a conventional manner.

An elongated balloon structure 54 is suitably formed on or mounted to the conduit 44 adjacent the distal end of the device and an inflation passage for the balloon 54 is defined longitudinally of the conduit and terminates proximally in an inflation port 56. The dilating needle-knife device 42 is adapted to be passed through the accessory channel of an endoscope. Thus, desirably, the conduit for the needle-knife wire 48 and the inflation passage for the balloon 54 define a profile that can be slidably accommodated in a standard endoscope accessory channel. Such a low profile dual passage conduit can be defined by concentric passages or side by side passages.

Figure 5:
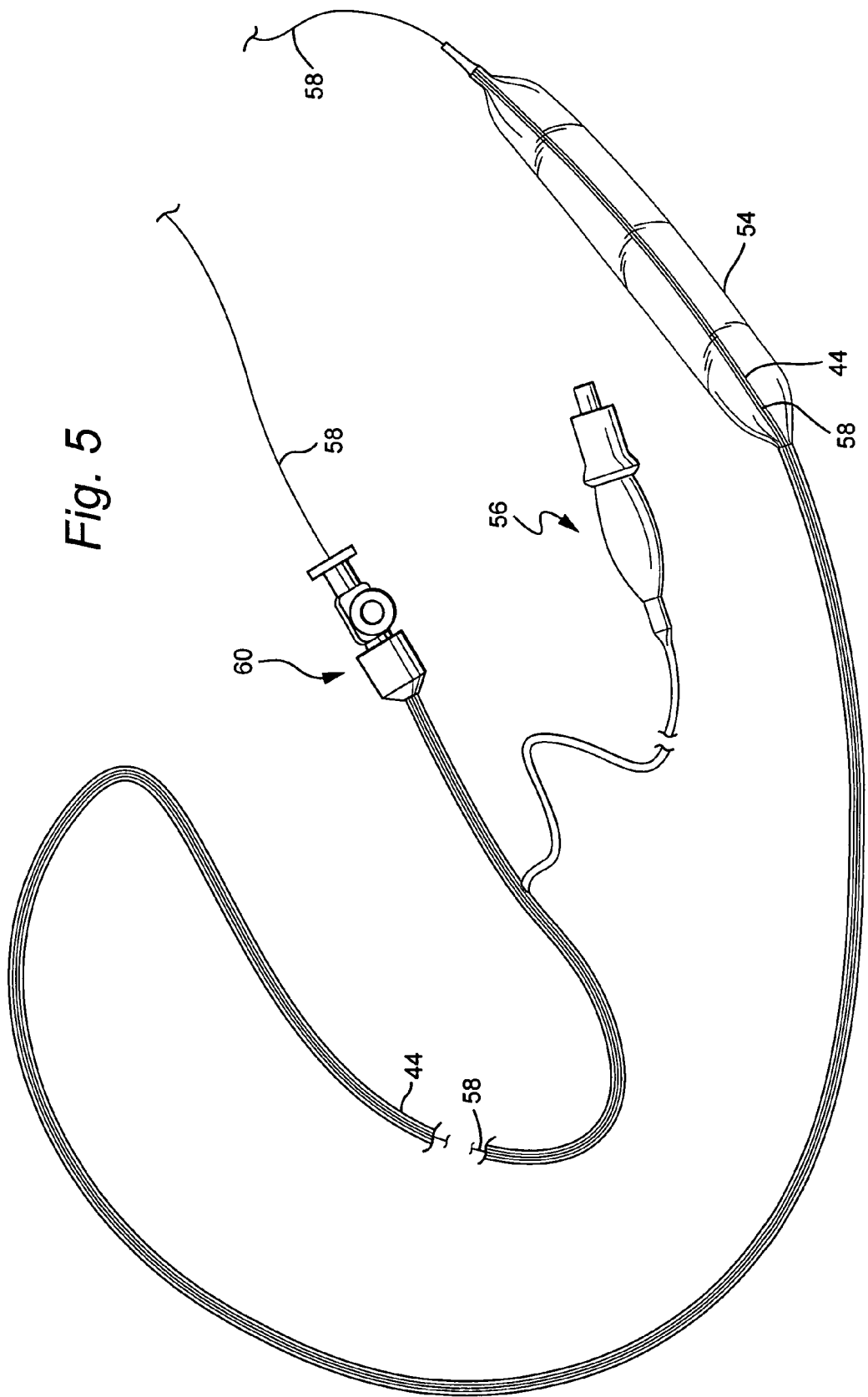
FIG. 5 is view of the needle-knife device of FIG. 3, with a guidewire substituted from the needle-knife wire and with the balloon inflated.

As explained in greater detail below, once an incision has been made by the needle-knife 48, care must be taken to avoid loss of the point or short line of incision during subsequent manipulation of the instruments. Accordingly, the dilating needle-knife device 42 is adapted for the selective removal of the needle-knife wire 48 and replacement thereof with a fine guide wire 58. Accordingly, once the incision has been made, the needle-knife 48 is retracted and the dilating needle-knife device 42 is advanced proximally so as to be disposed through the just formed incision. The needle-knife actuator 46 is then disengaged, i.e. unthreaded, from the proximal end 60 of the needle-knife conduit 44 and the needle-knife wire 48 withdrawn so that a find guide wire 58 can be accommodated in the conduit 44 of the needle-knife device 42. The guide wire 58 is advanced so as to protrude from the distal end of the needle-knife conduit 42, as shown in FIG. 5. Care is desirably taken to avoid excessive overfeed of the guide wire. To that end, the procedure may be fluoroscopically monitored and/or indicia may be provided on the guide wire so as to communicate to the surgeon the relative disposition of the guide wire 58 and the needle-knife conduit 44.

As noted above, the incision is desirably dilated to accommodate, e.g., the overtube 10. Accordingly, the dilating needle-knife device of the invention provides an elongated balloon 54 that may be selectively inflated while the needle-knife conduit is disposed to traverse the incision, thereby to dilate the same. In the illustrated embodiment, the dilating balloon 54 has a relatively low profile so as to avoid over dilation and the potential for tearing of the organ wall. The balloon is elongated in the illustrated embodiment so that the disposition of the needle-knife conduit 44 relative to the incision is less critical. In that regard, it is to be recalled that during the procedure, the incising and dilating procedure are observed through the endoscope 40 disposed in the overtube 10. However, during the dilating process, the visualization is limited to the gastric cavity side of the incision. The elongated balloon 54 also ensures that there will be uniform dilation of the stomach wall which may vary in thickness from patient to patient and from one locus to another. The length of the balloon is substantially greater than its diameter following inflation. More specifically, the balloon length is at least about twice the inflated diameter and more preferably about three to five times the inflated diameter, as shown in FIG. 5.

While the dilating needle-knife device 42 shown in FIG. 3 et seq has been described above in particular with reference to the process of incising the gastric wall to provide access to the peritoneal cavity and the dilation of the just incised wall, the dilating needle-knife device may be used in connection with a variety of other endoscopic procedures, including subsequent diagnostic and/or surgical procedures within the peritoneal cavity during transgastric peritoneoscopy. Indeed, the ability to sequentially incise and dilate using a single instrument to allow access to and selective passage into various organs and body passages minimizes the need to repeatedly exchange instruments through the accessory channel of the endoscope, thus reducing the steps of the procedure and minimizing the chance that the incision point will be lost. This potentially reduces the duration, cost and risks of the procedure.

As noted above, although the dilating needle-knife device we have developed can be used to substantial advantage according to the invention, as noted above, independent instruments may be sequentially used to accomplish the incising and dilating steps of the process. Thus, instead of the dilating needle-knife device described herein above, a conventional needle-knife can be fed through the accessory channel of the endoscope to the site to be incised, foot pedal or otherwise actuated to suitably heat the needle-knife which is then disposed relative to the target wall to form the desired incision. To locate and maintain the patency of the thus formed incision, the needle-knife is advanced through the incision. Thereafter according to the invention, so that dilation of the incision can be carried out, the needle-knife wire is removed from the needle-knife conduit and replaced by a guide wire as described in detail above. Then the needle-knife device is removed from over the guide wire and replaced with a dilating balloon catheter which is threaded over the guide wire, through the accessory channel of the endoscope, and through the incision. Finally the balloon catheter is inflated to effect the desired dilation of the incision.

As is evident from the foregoing, while the incising and dilating steps can be accomplished sequentially, with independent instruments sequentially exchanged and actuated, that process requires the provision of additional instruments and additional steps which can compromise the efficiency of the procedure and increase the risk of error.

Figure 7:
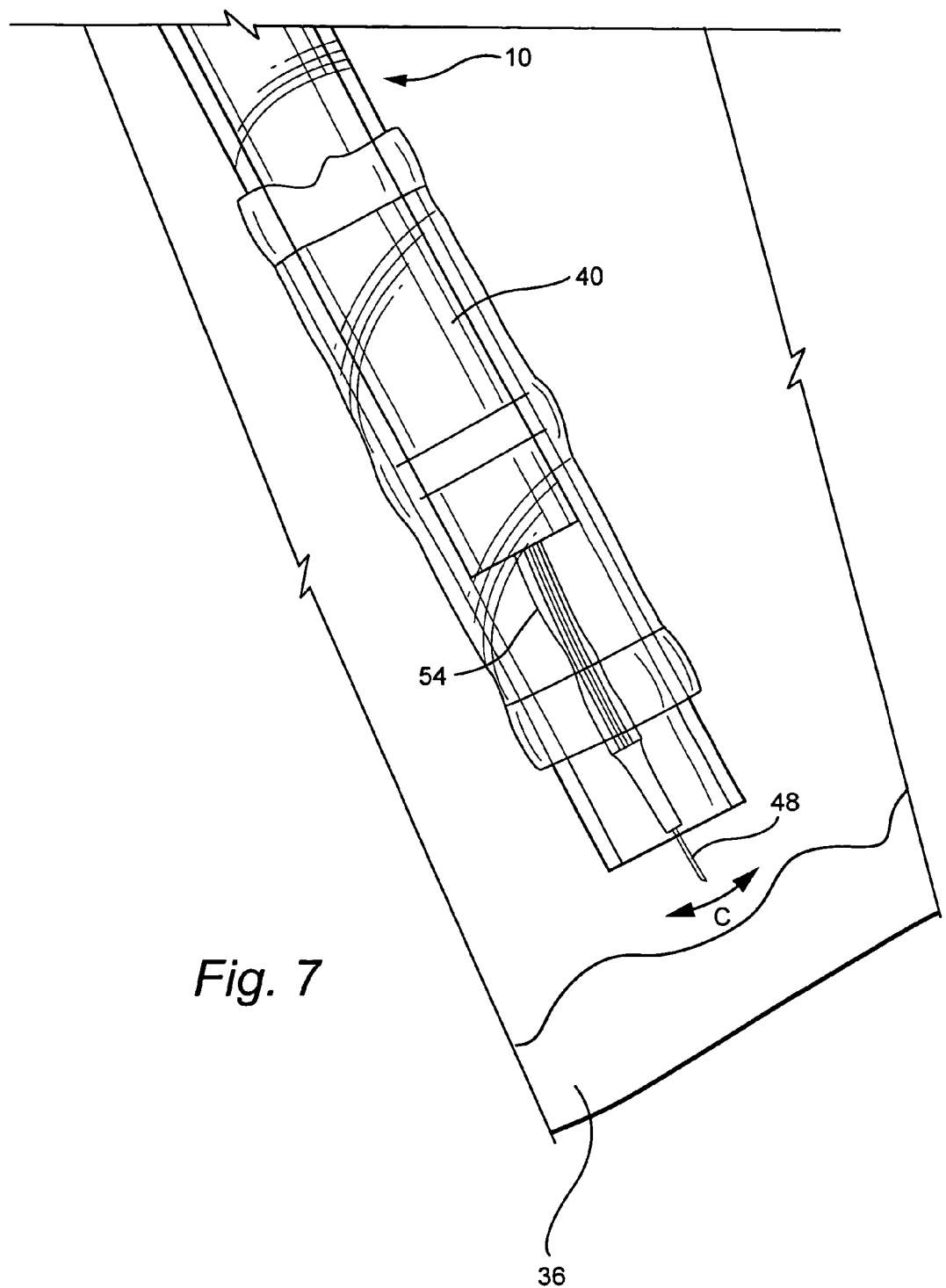
FIG. 7 is an enlarged view showing the needle-knife device disposed for incising the stomach wall to provide access to the peritoneal cavity.

As briefly described above with reference to FIG. 6, according to the invention, to gain access to the peritoneal cavity via the intestinal tract, a flexible overtube 10 of suitable length is introduced via the esophagus 34, or colorectally, preferably with an endoscope 40 disposed therewithin to steer and guide the overtube to a target portion of the digestive tract. Once so located, with the distal end of the overtube and endoscope in opposed facing relation to the target site for penetration through the wall of the digestive tract, an incising device, preferably the above-described dilating needle-knife device 42, is advanced through an accessory channel of the endoscope 40 so as to protrude beyond the endoscope. The needle-knife 48 is then actuated to protrude from the distal end of the needle-knife conduit 44 as shown in FIG. 7. The balloon 54 of the dilating device should be fully deflated before introduction through the endoscopic channel. The creation of a vacuum in the balloon with a syringe or the like applied to port 56 will thus facilitate insertion. A lubricant may be provided to the balloon 54 and outer surface of the device 42 to facilitate conduct to the target site through the endoscope 40. A silicone lubricant is preferred in that regard.

Once the needle-knife device is properly located, the incision line is determined and the needle-knife device is elevated using a conventional elevator associated with the accessory channel, or by displacing the entire distal tip of the endoscope 40, to move the needle-knife up and down the incision line as shown by arrow C in FIG. 7. The electrosurgical unit (not shown) is then actuated so that electric current flows to the needle-knife wire 48 thereby to substantially heat the needle-knife so that the instrument is ready to incise the stomach wall. Actuation may be effected in any desired manner, for example using a switch (not shown) provided on the actuator 46, with a foot pedal, or with another remote actuation device.

Figure 8:
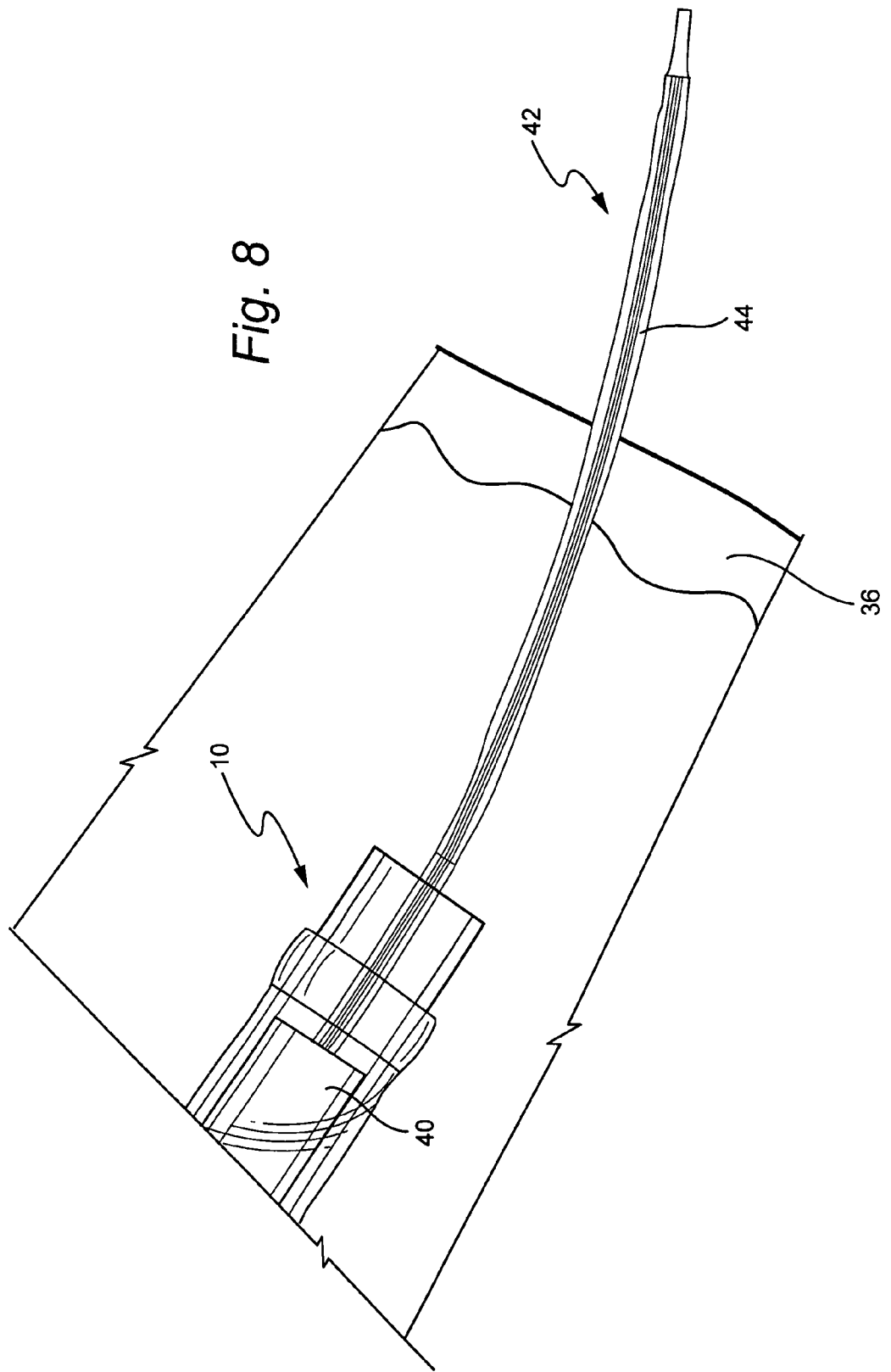
FIG. 8 is an enlarged view showing the needle-knife device displaced through the incision in the stomach wall, with needle retracted.

The needle-knife 48 is moved along the previously established incision line to simultaneously cut and cauterize the tissue. Once the incision has been completed while applying a continuous motion, the electrosurgical unit is turned off and the needle-knife 48 is retracted. Once the stomach wall has been incised, and the needle-knife retracted, the needle-knife device 42 is advanced so as to be disposed fully through the stomach wall as shown in FIG. 8. Again, the balloon of the dilating device should be fully deflated before introduction through the incision in the stomach wall. The needle-knife dilating device is advanced until the balloon is positioned essentially in the stricture defined by the incision through the gastric wall. Radiopaque markers may be incorporated on the conduit 44 and/or within the balloon 54 as visual markers for proper positioning.

Figure 9:
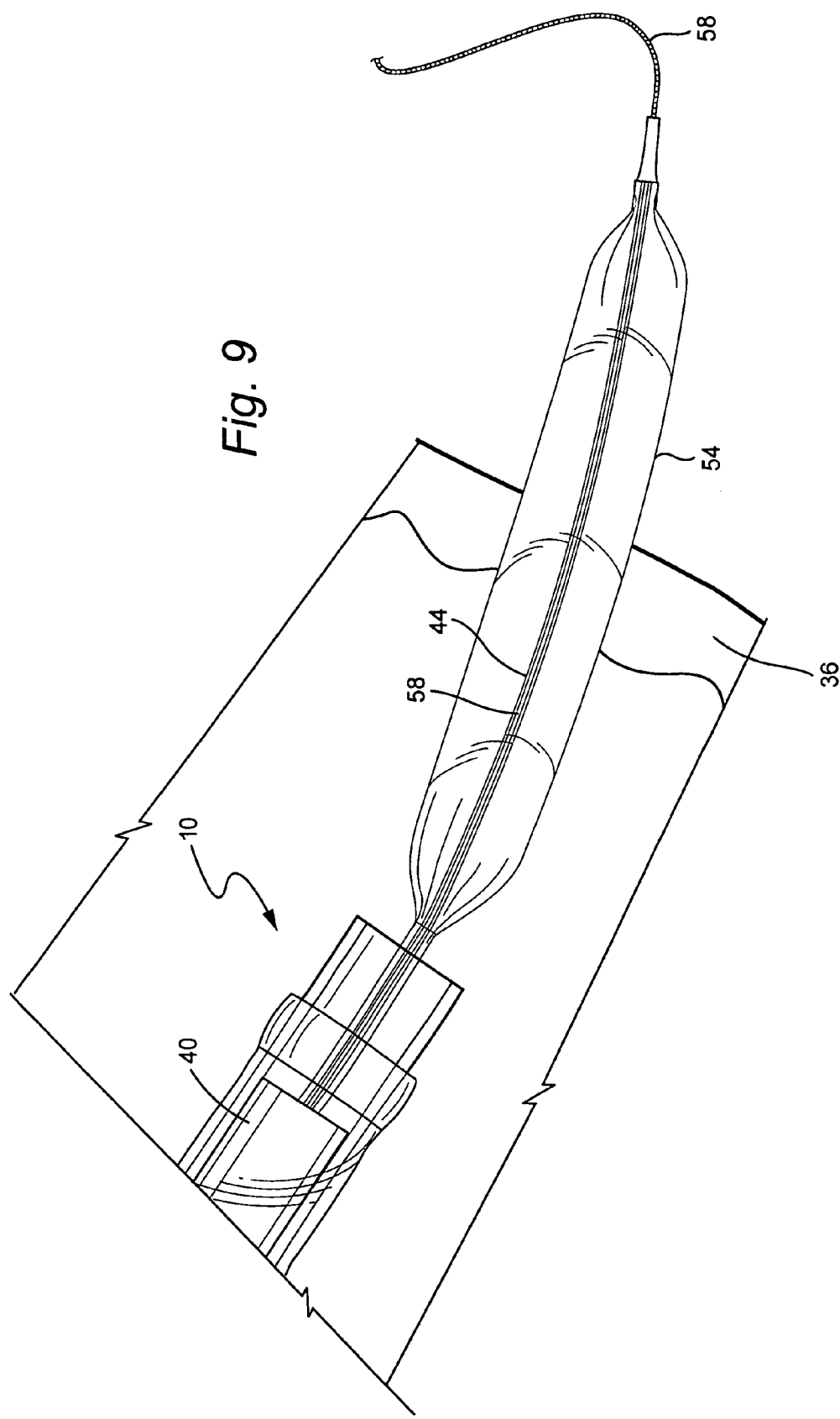
FIG. 9 is an enlarged view of the needle-knife device disposed through the incision in the stomach wall, with a guide wire disposed therethrough and with balloon inflated.

The needle-knife actuator 46 with attached needle-knife wire 48 is then removed from the needle-knife conduit 44 and a guide wire 58 is fed therethrough in its stead. Thus, in the unlikely event that the needle-knife is displaced so as to be removed from the incision in the stomach wall, the incision is located by the guide wire and the needle-knife device can be readily re-placed to complete its dilating function. Once the guide wire 58 has been fed through the needle-knife conduit 44 and the needle-knife device is disposed so that the balloon traverses the incision in the stomach wall 36, the balloon 54 is inflated, preferably while monitoring the balloon pressure using, e.g., a manometer, to effect a suitable dilation of the stomach wall, as shown in FIG. 9, to allow subsequent insertion of the overtube therethrough. Although the balloon 54 of the dilating device can be filled with air, it is preferably selectively filled with liquid. Liquid creates maximum radial pressure in the balloon for a more effective dilation of strictures. If desired, the balloon can be filled with a mixture of water or saline and contrast for fluoroscopic observation of the procedure.

Figure 10:
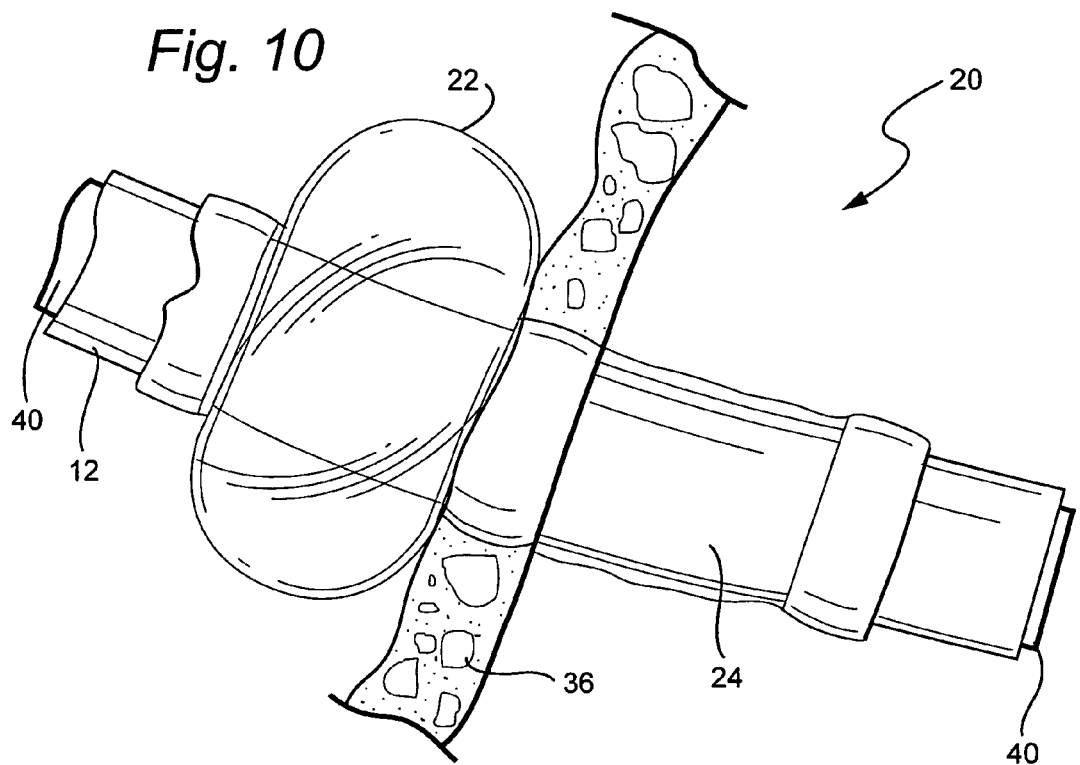
FIG. 10 is an enlarged view showing the overtube disposed through the stomach wall with one of the anchoring balloons inflated to limit overtube insertion.
Figure 11:
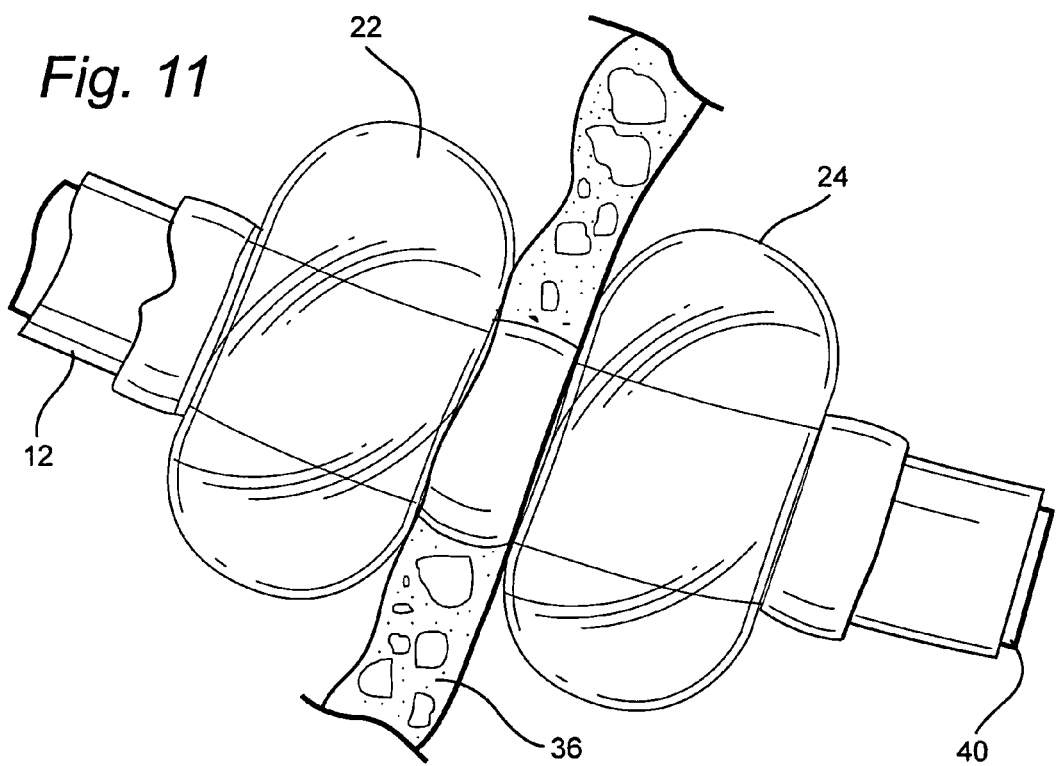
FIG. 11 is an enlarged view showing the overtube disposed through the stomach wall with both of the anchoring balloons inflated for anchoring the overtube to the stomach wall, thereby establishing a passage into the peritoneal cavity.

Once the dilating function has been achieved the dilating balloon 54 is deflated by applying suction to the balloon lumen via port 56. The overtube and endoscope are then advanced. Once the incision and dilating function of the dilating needle-knife have been completed, the needle-knife device 42 can be removed from the endoscope accessory channel and other instruments disposed therethrough in connection with diagnostic and/or therapeutic procedures to be performed within the peritoneal cavity thereafter. Once the overtube has been properly disposed to traverse the incision in the stomach wall, the balloons 22, 24 of the overtube 10 are inflated to anchor the overtube with respect to the gastric wall 36, as described hereinabove. As noted above, the proximal balloon 22 on the overtube conduit 12 may be inflated in advance of the distal balloon and indeed in advance of displacement of the overtube through the dilated incision in the stomach wall. Pre-dilating the proximal balloon 22 ensures that over insertion of the overtube 10 will be avoided (see FIG. 10). Avoiding over insertion is particularly desirable at this juncture as the peritoneal cavity has yet to be insufflated and thus it is desirable to avoid potential damage or injury to the structures within the peritoneal cavity that may result from over insertion. Once the overtube is in place, traversing the incision in the stomach wall, the distal balloon 24 is inflated to complete the anchoring process, as shown in FIG. 11. Although the balloons of the overtube can be filled with air, they are preferably selectively filled with liquid. Liquid creates maximum radial pressure in the balloon for a more effective anchoring of the overtube. If desired, the balloon can be filled with a mixture of water or saline and contrast for fluoroscopic observation of the procedure.

Figure 12:
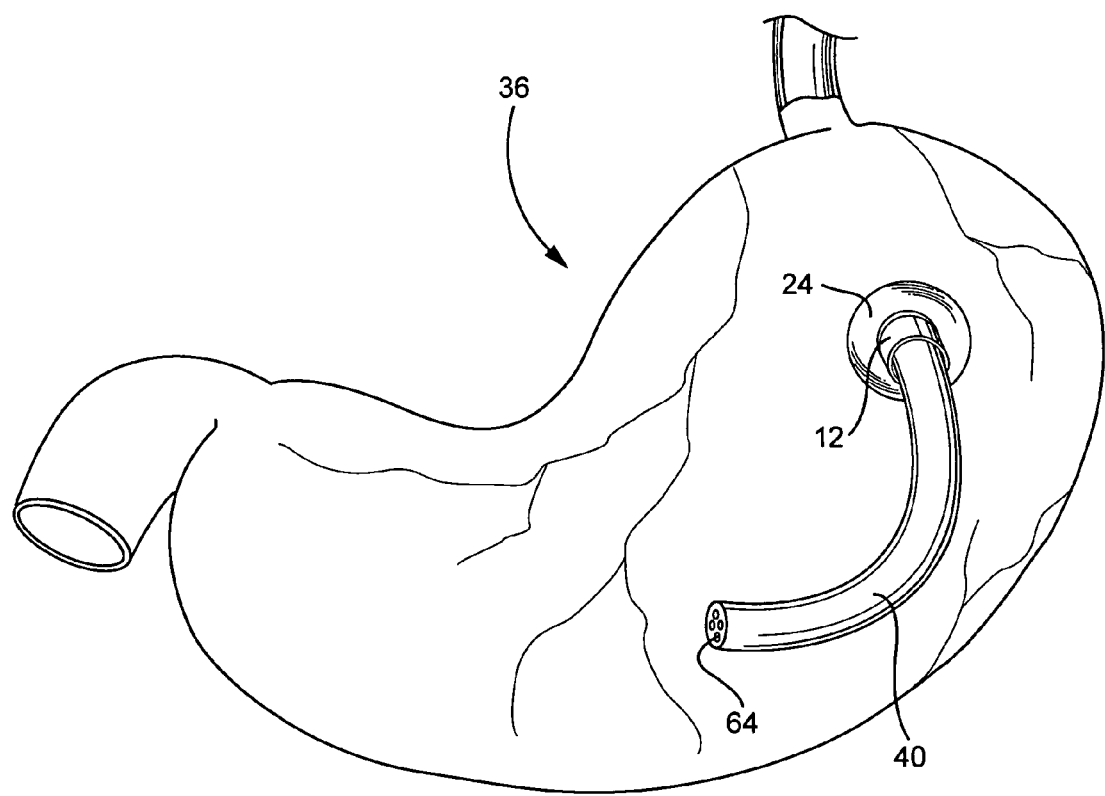
FIG. 12 is a perspective view showing the surface of the stomach with the overtube anchored thereto and an endoscope projecting from the overtube for visualizing, examining and/or conducting a surgical procedure in the peritoneal cavity.

Once the overtube has been suitably anchored with anchoring balloons 22, 24, or other anchoring mechanism, the endoscope 40 may be advanced beyond the distal end of the overtube as shown in FIG. 12 so that the structures disposed within the peritoneal cavity can be observed, e.g., for diagnostic purposes. As with conventional endoscopic intra-abdominal procedures, gas is desirably injected via the endoscope to insufflate the peritoneal cavity to enable e.g., manipulation of the endoscope and a clear view of the structures of interest within the peritoneal cavity. Additional media can be injected via port 62 in valve housing 14, as deemed necessary or desirable. Once the endoscope has been thus disposed, a variety of endoscopic procedures can be carried out in the manner similar to procedures conducted during Laparoscopy. Thus, a variety of diagnostic, therapeutic and/or surgical accessories may be fed through the accessory channel(s) 64 of the endoscope, and dissected tissue and the like removed therethrough. In the even material is too voluminous to be readily extracted through the accessory channel 64 of the endoscope 40, it can be severed and clamped at the end of the endoscope and removed through the larger diameter overtube 10. The endoscope 40 can then be re-placed for subsequent visualization and procedures.

As is evident, a variety of surgical procedures can be performed using the transgastric approach described herein above. For example, procedures such as biopsy, the lysis of adhesions, the application of the ligating clips to fallopian tubes for tubal ligation purposes, providing anastomotic couplings between adjacent segments of intestine or between the stomach and the portion of the intestine to bypass a diseased organ segment, gallbladder removal (which is discussed in greater detail below), appendectomy, hysterectomy, and/or other organ removal, and similar such surgical procedures. If additional viewing or instrument delivery is desired beyond that which can be provided though a single overtube, a second overtube can be fed through the digestive tract, colorectally. Thus, it can be seen that with the peritoneal access approach disclosed herein above, at least two passages for endoscopes and instruments can be provided so as to accommodate virtually any micro-surgical procedure within the peritoneal cavity.

Once the intra-abdominal procedure has been completed, the endoscope 40 is retracted into the overtube 10 and at least the distal balloon 24 of the overtube 10 is deflated by applying suction to the inflation port 28. The overtube and endoscope therewithin are then retracted in the illustrated example into the gastric cavity whereupon, if not previously deflated, the proximal balloon 22 of the overtube 10 is preferably deflated as well. At this point, however, an incision 66 in the gastric wall remains and must be closed, preferably with a mechanical fastener, to complete the procedure. In accordance with a preferred embodiment of the invention, clip fixing devices 68 are used to close the incision. More specifically, clip fixing device applicators 70 for passage through the accessory channel 64 of an endoscope 40 and clip fixing devices 68 of various sizes are commercially available. Since clip fixing devices 68 are among the most easily manipulated and applied of the currently available endoscopically applied ligating devices, the use of clip fixing devices 68 to close the incision 66 is presently preferred. However, other mechanical fasteners such as sutures, staples and other commercially available ligating devices can be applied endoscopically, and/or another incision closing process or procedure can be used as deemed necessary or desirable to close the incision.

Figure 13:
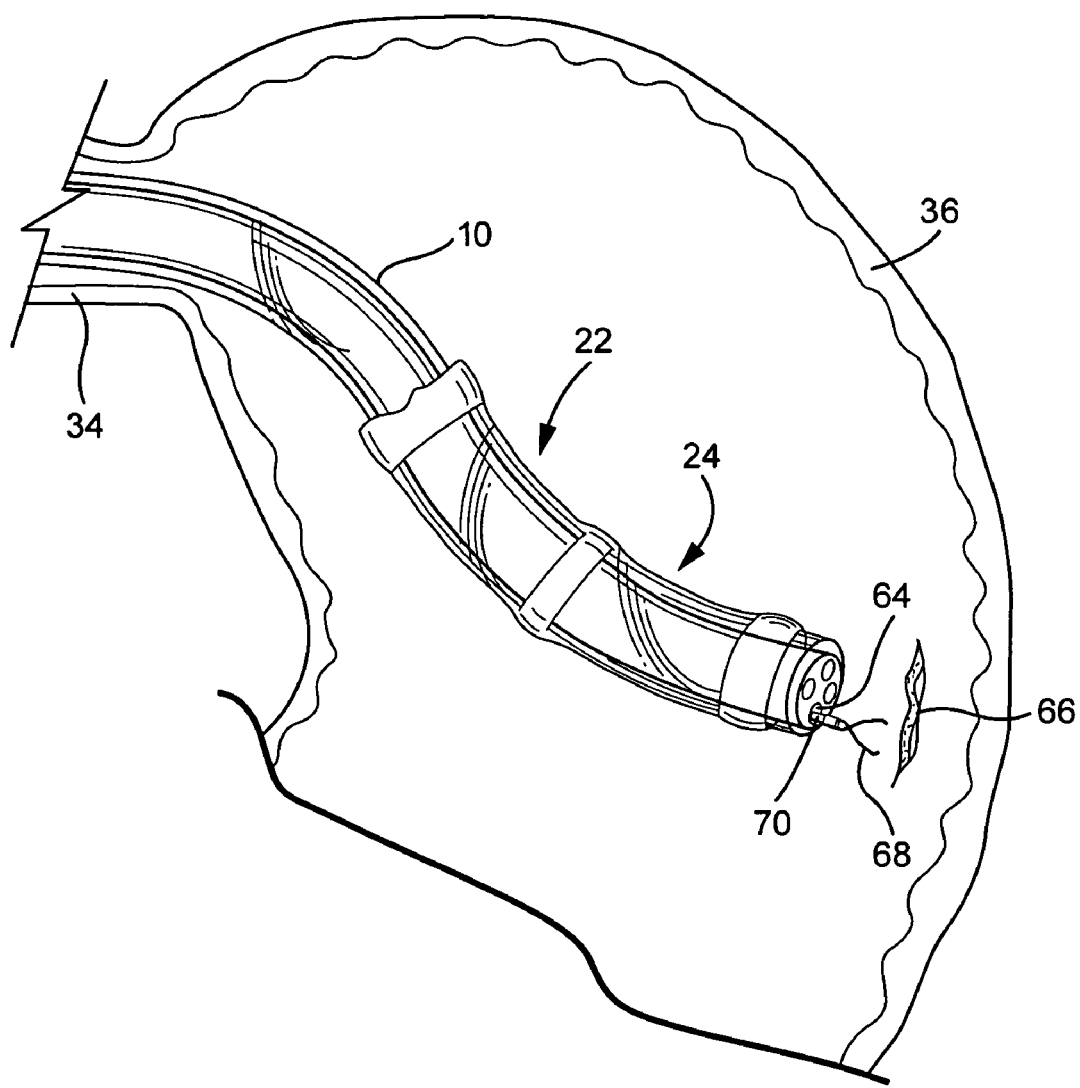
FIG. 13 is a schematic view showing the endoscope ready to apply clip fixing devices to close the incision in the gastric wall at the conclusion of the procedure.
Figure 14:
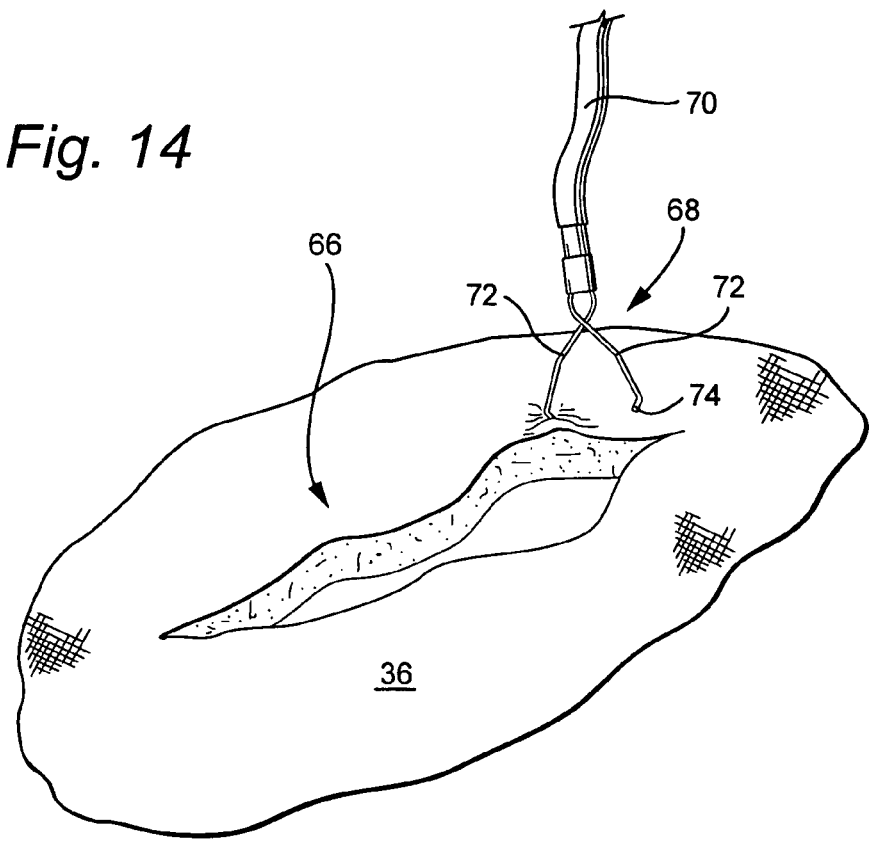
FIG. 14 is a schematic view showing a clip fixing device engaging a side of the incision as a step in the clipping process.
Figure 15:
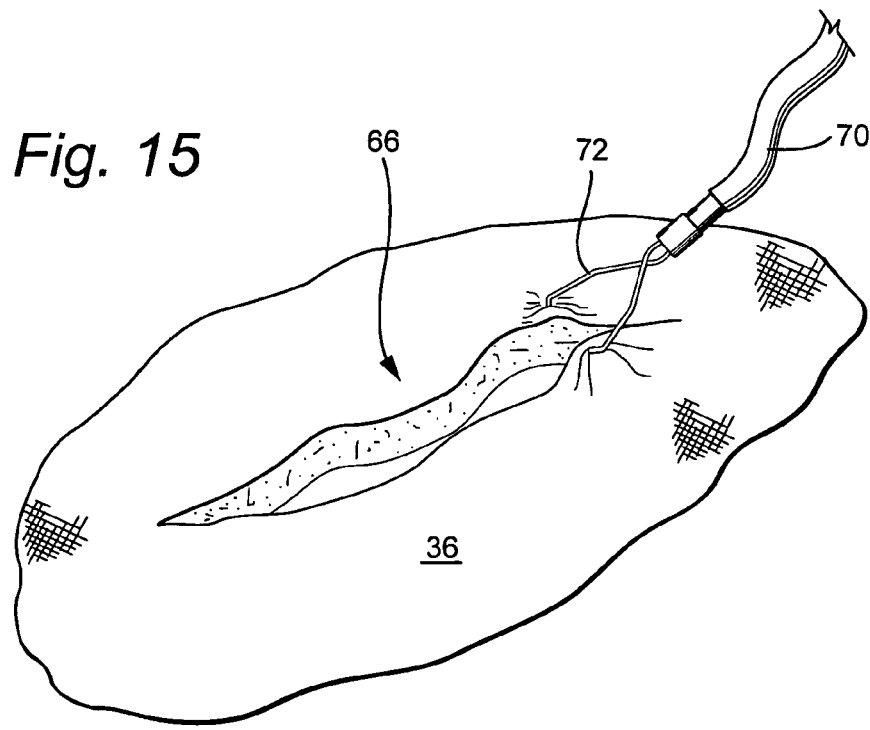
FIG. 15 is a view similar to FIG. 14 showing the clip fixing device engaging both sides of the incision, prior to closing the clip.
Figure 16:
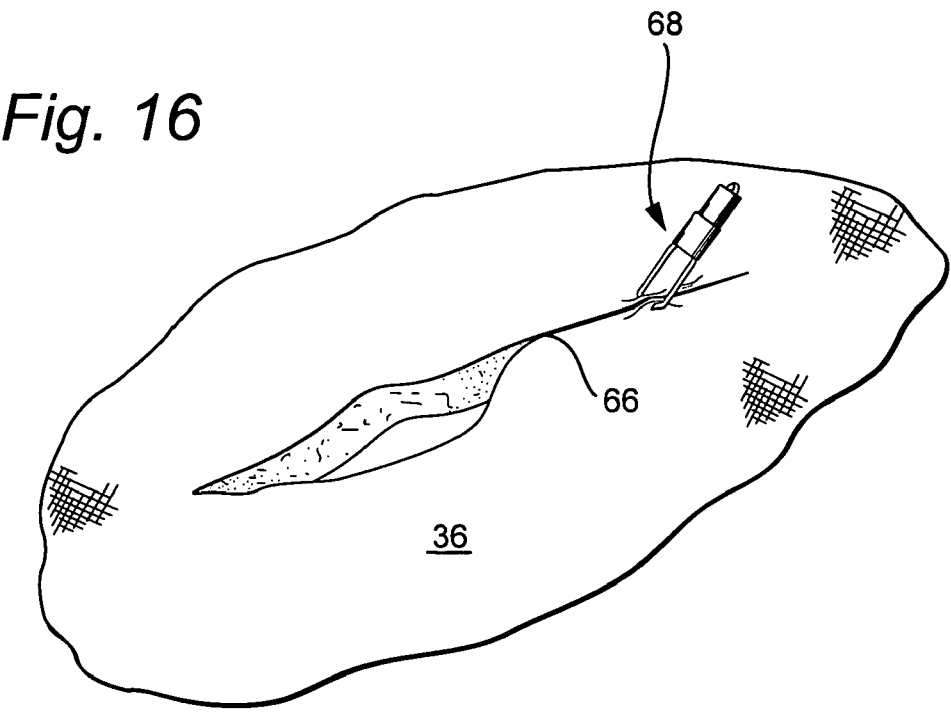
FIG. 16 is a schematic view showing the clip fixing device closed to close a part of the incision.
Figure 17:
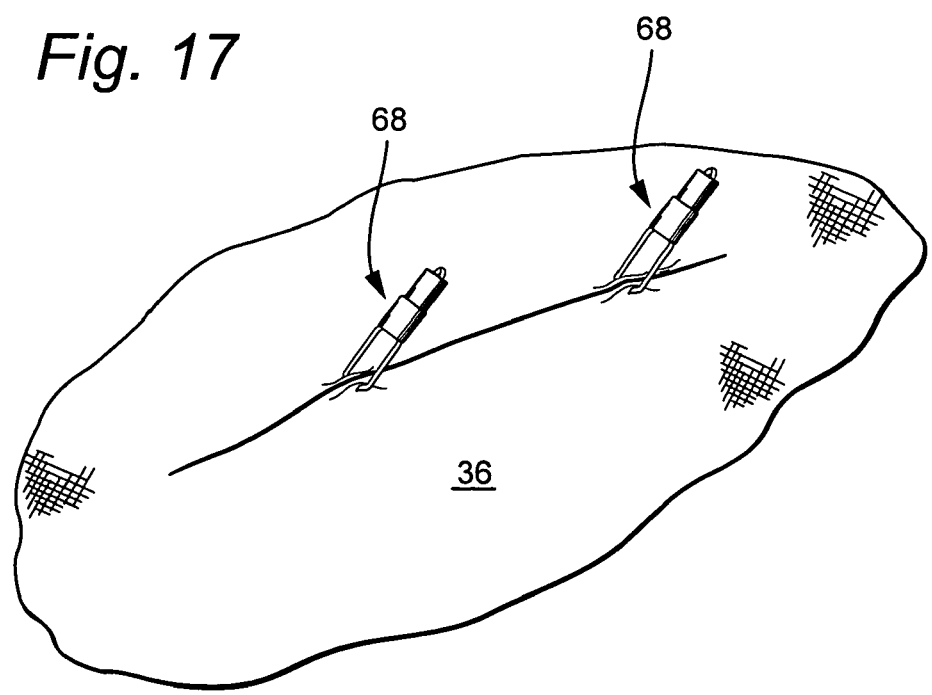
FIG. 17 is a schematic view showing clip fixing devices applied side by side to close the incision in accordance with an exemplary embodiment.

FIG. 13 schematically illustrates the distal end of the endoscope 40 with a loaded clip fixing device applicator 70 projecting therebeyond, poised for application to close the incision 66 remaining after removal of the overtube 10 from the gastric wall. The clip fixing device 68 includes first and second arms 72 terminating in a tissue gripping structure 74. To close the incision, the distal end of one clip fixing device arm is contacted so as to engage the tissue on one side of the incision 66, as shown in FIG. 14. Then, as shown in FIG. 15, the clip fixing device 68 is manipulated so that the distal end of the other clip arm engages the tissue on the opposite side of the incision 66 so that the clip 68 is engaged with tissue on both sides of the incision. The clip fixing device actuator 70 is then actuated to close the clip fixing device 68 and clamp the tissue therebetween so as to close the associated portion of the incision, as shown in FIG. 16. Depending upon the size of the incision 66, one or more additional clip fixing devices 68 may be applied. In the illustrated embodiment (FIG. 17) a second clip fixing device 68 is applied to securely close the incision.

EXAMPLE

We evaluated the feasibility, efficacy and safety of an endoscopic trans-gastric approach to the peritoneal cavity in a porcine model with long-term survival. Methods: 45-50 kg pigs had initial endoscopic needle-knife incisions of the gastric wall followed by balloon dilation/electrocautery of incision under general anesthesia using sterile techniques. Antibiotic irrigation of stomach was performed prior to initial incision for pigs #3,4,5. The endoscope underwent high level disinfection followed by gas sterilization and was advanced via sterile overtube into the peritoneal cavity for peritoneoscopy and liver biopsy. The gastric incision was subsequently closed with clip fixing devices. The pigs were sacrificed at 14 days. Peritoneal cultures, endoscopic and pathologic examinations were performed.

Results: 5 pigs had gastric incisions that were easily performed with rapid access to the peritoneal cavity using a sterile endoscope. Insufflation of the peritoneal cavity was quick and the view of the intra-abdominal organs was spectacular. The intra-abdominal and pelvic organs were readily seen and accessed for complete examination. Directed liver biopsies were easily performed and closure of gastric incision was successful in all pigs. All pigs were able to tolerate a regular diet within 24 hours, eat heartily and thrive over the next 14 days with a mean weight gain of 7.1 pounds (±2.6 pounds, 95% C.I. (3.87,10.3). Endoscopic follow-up of the stomach was normal. 4/5 pigs had negative follow-up cultures. 1/5 pig had Proteus sp. Grossly, 2/5 pigs had normal stomachs, pathologically 2/5 pigs had microabscesses (pigs #1,2) and 1/5 pig had remote inflammation only. None of the pigs that had antibiotic irrigation of the stomach developed microabscesses.

Conclusion: This study is the first to show that the transgastric endoscopic access of the peritoneal cavity with prolonged survival is feasible in the porcine model. This suggests that the endoscopic/transgastric approach to the peritoneal cavity may have potential for a wide range of surgical interventions.

Flexible endoscopic surgery and examination have been described above with reference to accessing the peritoneal cavity through the wall of the digestive tract for examination and surgical procedures. One such surgical procedure is flexible endoscopic cholecystectomy (FEC) which refers to the removal of the gall bladder via the digestive tract using the flexible endoscope. More particularly, FEC proposes to access the peritoneal cavity via the digestive tract and, in particular, the intestinal wall, in this case rather than the stomach wall for excision and removal of the gall bladder. The steps involved in this procedure would include insertion of the endoscope into the intestines, incision through the bowel wall for passage of the endoscope into the peritoneal cavity, removal of the gall bladder, closure of the intestinal wall incision and removal of the endoscope.

Since the first cholecystectomy in 1882, the procedure has become widespread with over 500,000 performed annually in the United States alone. The safety of this procedure has improved with the overall mortality rate decreasing from 6.6.% in 1932 to 1.8% in 1952 and 0.17% in 1989 with a general complication rate around 4.4-4.9%. A major disadvantage of this procedure is the need for a relatively large incision of skin, subcutaneous fat tissue, and abdominal wall muscles leading to prolonged healing of the postoperative wound with significant pain and disability. Furthermore, large incisions are associated with an increased risk of infection and development of postoperative hernias.

Laparoscopic cholecystectomy was reported first in the late 1980s and was an attractive option because of the smaller incisions used. Initially, it was used only sporadically in few centers in Europe because of the novelty of this unfamiliar approach to cholecystectomy in the United States. However, with advances in laparoscopic instrumentation and the obvious advantages of microsurgical technique over open surgery (small skin incision, minimal injury to the tissues, short postoperative hospital stay, etc.), there was widespread acceptance of laparoscopic cholecystectomy as the ideal technique for cholecystectomy. Although the mortality rate is low 0.07% a major drawback remains the necessity of entering into peritoneal cavity via at least 3 separate skin incisions, resulting in postoperative scars, possible infection and postoperative hernias.

We propose FEC as the next step in the development of minimally invasive cholecystectomy. This procedure will consist of upper endoscopy via an already existing natural entrance (mouth), incision of the gastric or intestinal wall to enter the peritoneal cavity, removal of the gallbladder and closure of the incised wall. Thus, FEC will not require skin incision. This will result in a perfect cosmetic effect, entirely eliminating the possibility of postoperative hernias. As nerves and muscles of abdominal wall will not be incised, FEC will be painless. This makes FEC potentially an outpatient procedure.

In the state of Maryland alone, 9993 cholecystectomies were performed in 1992. In 1996 the average total charge for an in-hospital laparoscopic cholecystectomy was $13,940 and $15,380 for an open cholecystectomy. Average length of stay for a laparoscopic cholecystectomy was 3.37 days and was 6.12 days for open cholecystectomy.

Flexible endoscopic cholecystectomy is evidently a less invasive procedure than traditional cholecystectomy with a expected reduction in post-operative morbidity such as abdominal pain. As a minimally invasive procedure, flexible endoscopic cholecystectomy (FEC) may theoretically be performed on an out-patient basis and at least realize a shortened or no-hospital stay. The reduced hospital stay and less invasive characteristics of the procedure would produce a significant cost saving as compared to existing laparoscopic and surgical cholecystectomy. Moreover, the absence of external scars make the procedure cosmetically perfect.

The instruments preferably utilized for this procedure include the instruments described above. More specifically, the instrument proposed for performing FEC include a flexible peritoneoscope which is actually the two-part assembly described above including on the one hand a flexible endoscope 40 with large accessory channel(s) 64 for the passage of micro-surgical devices and an outer sheath or overtube 10 for maintaining sterility of the endoscope and defining a path for the endoscope from outside the patient's oral cavity to and through the wall of the digestive tract.

An endoscopic knife is a further instrument required for the implementation of this surgical procedure for making an incision in the bowel wall and for assisting in excision of the target tissue, such as the gallbladder. The endoscopic knife is preferably electro-cautery to minimize bleeding following incision. This instrument may additionally have a video chip for additional imaging. Various accessories are further provided for the peritoneoscope, such as endoscopic dissecting forceps for dissection and ligation of the cystic artery, veins, and cystic duct; an endoscopic clip applicator other suturing or ligating device to ligate vessels, close tissue planes and close the bowel incision; and grabbing forceps for extraction of the gallbladder and/or other target tissue.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for accessing an interior of a cavity of a mammal, said method comprising:
   positioning an elongated flexible conduit to extend from an exterior of the mammal through a natural orifice into and along at least a portion of the digestive tract to a target wall segment in the digestive tract;
   forming an incision in said target wall segment;
   advancing a distal end of said flexible conduit so that the distal end of said conduit extends through said wall;
   after forming said incision and advancing the distal end of said flexible conduit through said wall, anchoring said distal end with respect to said wall;
   advancing an endoscope through said conduit so that a distal end of said endoscope is disposed adjacent or distal to said distal end of said conduit;
   viewing at least one of a tissue and an organ within said cavity;
   releasing said anchor;
   withdrawing said conduit and said endoscope through said wall; and
   closing said incision,
   further comprising, after said forming an incision and before said advancing said conduit, dilating said incision to facilitate passage of said conduit therethrough, wherein said dilating comprises dilating with an inflatable balloon.

2. A method as in claim 1, wherein an endoscope is disposed within said conduit during said positioning step and wherein said endoscope is manipulated to guide and direct said flexible conduit to said target wall segment.

3. A method as in claim 1, wherein said flexible conduit has a pair of anchoring balloons defined adjacent a distal end thereof, and wherein said anchoring comprises inflating said anchoring balloons so that a proximal said balloon is disposed within said digestive tract and a distal said balloon is disposed in the cavity, thereby to capture said wall therebetween.

4. A method as in claim 1, wherein said target wall segment is a portion of the stomach wall.

5. A method as in claim 1, wherein said positioning said flexible conduit comprises positioning said flexible conduit through the patient's oral cavity and esophagus.

6. A method as in claim 1, wherein said method is performed in the absence of an incision in the abdominal wall.

7. A method as in claim 1, wherein said cavity is the peritoneal cavity.

8. A method as in claim 7, wherein a proximal end of said flexible conduit comprises a valve housing including a valve structure for defining a substantially air tight seal about said endoscope disposed therethrough and having a gas injection port, and wherein said method further comprises injecting a gas through said gas injection port so as to insufflate the peritoneal cavity after said anchoring step.

9. A method as in claim 1, further comprising, after said viewing, performing at least one endoscopic surgical procedure in said cavity.

10. A method as in claim 9, wherein said at least one surgical procedure comprises organ removal.

11. A method as in claim 1, wherein said closing comprises applying a mechanical fastener to at least partly close said incision.

12. A method as in claim 11, wherein said applying comprises applying a ligating clip to close at least a portion of said incision.

13. A method as in claim 12, wherein said applying comprises disposing a clip applicator through an accessory channel of said endoscope, engaging a clip disposed at a distal end of said clip applicator with tissue on each lateral side of said incision and actuating said clip so as to clamp said tissue and close said incision.

14. A method as in claim 1, wherein said forming comprises forming an incision with an endoscopic knife device.

15. A method as in claim 14, further comprising, after said forming, advancing a distal end of said endoscopic knife device through said incision.

16. A method as in claim 14, wherein said endoscopic knife device comprises a needle-knife, and wherein said forming comprises cutting said target wall segment with said needle-knife.

17. A method as in claim 16, wherein said endoscopic knife device is operatively coupled to an electrical source for heating said needle-knife and further comprising actuating said electrical source to heat said needle-knife.

18. A method as in claim 16, wherein said endoscopic knife device further comprises a conduit within which said needle-knife is disposed, and wherein said needle-knife can be selectively extended to project from a distal end of said conduit and selectively retracted so as to be disposed within said conduit and wherein said needle knife is mounted so as to be selectively removable through a proximal end of said needle-knife conduit and wherein said method further comprises, before said forming, extending said needle-knife to project from said distal end of said conduit, and after said forming step retracting said needle-knife.

19. A method as in claim 18, further comprising, after said forming, advancing the distal end of said endoscopic knife device through said incision.

20. A method as in claim 19, further comprising removing said needle-knife from said needle-knife conduit and feeding a guide wire through said needle-knife conduit.

21. A method as in claim 20, wherein said endoscopic knife device further comprises an inflatable balloon provided adjacent said distal end of said needle-knife conduit, and further comprising, after said advancing of said endoscopic knife device through said incision, inflating said inflatable balloon to dilate said incision.

\* \* \* \* \*